(12) United States Patent
Termanini

(10) Patent No.: US 8,622,896 B1
(45) Date of Patent: Jan. 7, 2014

(54) LIQUID-COOLED LIGHT SOURCE FOR ENDOSCOPY AND IRRIGATION/SUCTION AND POWER SUPPLY TUBING AND METHOD THEREOF

(71) Applicant: Zafer Termanini, Boca Raton, FL (US)

(72) Inventor: Zafer Termanini, Boca Raton, FL (US)

(*) Notice: Subject to any disclaimer, the term of this patent is extended or adjusted under 35 U.S.C. 154(b) by 0 days.

(21) Appl. No.: 13/734,919

(22) Filed: Jan. 4, 2013

(51) Int. Cl.
*A61B 1/06* (2006.01)
*A61B 1/04* (2006.01)
*G02B 21/28* (2006.01)
*A61B 1/12* (2006.01)

(52) U.S. Cl.
CPC . *A61B 1/12* (2013.01); *A61B 1/128* (2013.01); *A61B 1/0661* (2013.01); *A61B 1/0669* (2013.01); *A61B 1/0684* (2013.01); *Y10S 362/80* (2013.01)
USPC ........... 600/178; 600/179; 600/158; 600/109; 600/112; 600/156; 348/65; 362/580; 362/800

(58) Field of Classification Search
CPC ........ A61B 1/12; A61B 1/128; A61B 1/0661; A61B 1/0669; A61B 1/0684; A61B 1/0692
USPC ......... 600/112, 109, 156, 158–159, 178–179; 348/65, 72; 396/17; 362/218, 294, 580, 362/800
See application file for complete search history.

(56) References Cited

U.S. PATENT DOCUMENTS

| | | | |
|---|---|---|---|
| 6,480,389 B1* | 11/2002 | Shie et al. | 361/707 |
| 2006/0173244 A1* | 8/2006 | Boulais et al. | 600/156 |
| 2009/0076328 A1* | 3/2009 | Root et al. | 600/131 |
| 2009/0299137 A1* | 12/2009 | Gal et al. | 600/109 |
| 2010/0177519 A1* | 7/2010 | Schlitz | 362/294 |
| 2011/0295072 A1* | 12/2011 | Boulais et al. | 600/176 |
| 2013/0131451 A1* | 5/2013 | Dillinger et al. | 600/127 |

* cited by examiner

*Primary Examiner* — John P Leubecker
*Assistant Examiner* — Arnaldo Torres Diaz
(74) *Attorney, Agent, or Firm* — Norris McLaughlin & Marcus, PA

(57) ABSTRACT

A liquid cooled endoscopy unit having plurality of LED light source units integrated into the proximal end of the arthroscope. The LED light source is cooled by the sterile conventional irrigation fluid circulating inside a cooling chamber located in the body of the arthroscope and conveniently capable on demand of emitting UV light for fluorescein endoscopy. The inventive device conveniently incorporate and contains all tubing and power supply cables for the camera and LED light source in a single tubing.

14 Claims, 6 Drawing Sheets

LIQUID-COOLED LIGHT SOURCE FOR ENDOSCOPY AND IRRIGATION/SUCTION AND POWER SUPPLY TUBING AND METHOD THEREOF

BACKGROUND OF THE INVENTION

The disclosure relates generally to medical imaging devices used during surgical procedures to visualize a surgical area, and more particularly, to an endoscopy device having a single unitary non-slip tubing for irrigation, suction, electrical power, imaging data, and the thermal management of integral Light Emitting Diode (LED) light sources using liquid filled cooling chamber.

Typically, a health care provider may use endoscopy for the investigation of symptoms, confirmation of a diagnosis, or for giving treatment. Generally, endoscopy is used to visualize and explore an anatomical cavity. Endoscopy, when directed toward a specific anatomical application, may be referred to by terminology specific to the endoscopic application. For example, arthroscopy is generally used to visualize and explore a large joint such as the knee, hip, or the shoulder or smaller joints such as the wrist, elbow, and ankle. Accordingly, arthroscopy helps eliminate the need for conventional and relatively invasive surgery on the joints. The terms arthroscopy and endoscopy are used interchangeably and both generally relate to medical imaging devices used during surgical procedures to visualize a surgical area.

Conventional arthroscopy entails insertion, under anesthesia, of a probe into a joint to be examined. The probe assembly typically comprises a high-definition camera and a light source. Conventional arthroscopy light sources generate light using halogen bulbs, which generate an excessive amount of heat. Excessive heat is usually managed with a fan. Said light source is attached to a fiber-optic cable to transmit the light from the light source to the arthroscope. The joint is usually distended for better visualization of the interior structures of the anatomical cavity, which is accomplished by injecting sterile irrigation fluid. Said irrigation fluid is injected into the joint through irrigation portals. The rate of flow and the pressure of the fluid are controlled by the surgeon. The irrigation fluid is subsequently sucked out under vacuum and through suction channels conveniently located into the arthroscope shaft. The suction and irrigation tubing as well as the power cable for the high definition camera are assembled at the time of surgery and connected to the appropriate units. However, they are laid down onto the surgical field, which becomes congested with several cables and wires, which may become entangled, or slide off the operative field and become contaminated. The plurality of tubing and cables attached to the arthroscope may also become cumbersome and reduce the dexterity of the surgeon.

That main problem with conventional arthroscopy unit is that the halogen light source becomes excessively hot requiring a fan or other cooling process. Furthermore, the fiber optic light transmission cable is fragile and sustains considerable damage from repetitive sterilization process causing breakage of the individual sintered fibers and progressive loss of the transmitted light intensity. U.S. Pat. No. 7,668,450 describes the use of multiple LED light sources. However, they seem to generate a substantial amount of heat, which requires a cooling device such as an external heat sink and a Peltier device. These can be cumbersome and expensive. They may get considerably hot themselves and may inflict injury to the operator.

US Pat. Application Publication 2008/0064931 A1 describes one or more channels which may carry cooling fluid. However, the LED elements are mounted on aluminum or ceramic plate or substrate, which is bonded to the cooling channel. There is no direct contact of the cooling fluid with the LED elements, Furthermore; the fluid is directed across the imaging lenses to clear body fluid or tissue debris.

While these devices may be suitable for the particular purpose to which they address, they are not suitable for providing a liquid cooled integral LED light source for endoscopy.

A major improvement provided by the instant invention is a single tube comprising irrigation/suction tubes, cable and LED power supply cable for the camera all in a singular non-slip tube attached to the outer scope unit with a simple "Quick Connect" mechanism.

BRIEF SUMMARY OF THE INVENTION

In view of the forgoing disadvantages inherent in conventional endoscopy units now present in the prior art, the present invention provides a new liquid cooled endoscopy unit having a single irrigation and suction tubing construction and a light source capable conveniently of emitting UV light for the purpose of fluorescein endoscopy.

The general purpose of the present invention, which will be described subsequently in greater detail, is to provide a new liquid cooling chamber to reduce the heat generated by the integral LED light source during an arthroscopic procedure. Furthermore, the present invention describes an endoscopy unit having single tubing for housing the power supply, camera cable and irrigation and suction drains. The new system has many of the advantages of the conventional endoscopy unit and many novel features that result in a new liquid cooled endoscopy unit comprising a single housing for irrigation suction tubing and power supply cords, which is not anticipated, rendered obvious, suggested or even implied by any of the prior art conventional arthroscopes and is, either alone or in any combination thereof.

To attain this, the present invention generally comprises an circular LED base containing plurality of LED elements. Said circular base having a hollow core to allow sterile irrigation fluid commonly used in endoscopy procedures to circulate through and come in direct contact with the waterproofed LED elements thereby reducing any heat generated by the LED light source Unit. Said cooling chamber comprises ingress and egress irrigation channels as well as quick connect attachments for the LED power supply and camera power data cable and power supply. The LED unit comprises one or more LED light elements capable of providing sufficient white light for ease of viewing. The LED unit can also provide on demand ultraviolet blue light for fluorescein endoscopy. This being very helpful in detecting small and superficial damage to the articular cartilage that can be missed with strong conventional white light. This technique is widely used by ophthalmologists to detect superficial corneal abrasions.

There has thus been outlined, rather broadly, the more important features of the present invention in order that the detailed description thereof may be better understood, and in order that the present contribution to the art may be better appreciated. There are additional features of the invention that will be described hereinafter.

In this respect, before explaining at least one embodiment of the present invention in detail, it is to be understood that the invention is not limited in its application to the details of construction and to the arrangements of the components set forth in the following description or illustrated in the drawings. The invention is capable of other embodiments and of being practiced in out in various ways. Also, it is to be understood that the phraseology and terminology employed herein are for the purpose of the description and should not be regarded as limiting.

Other objectives and advantages of the present invention will become obvious to the reader and it is intended that these objects and advantages are within the scope of the present invention.

To the accomplishment of the above and related objects, this invention may be embodied in the form illustrated in the accompanying drawings, attention being called to the fact however, that the drawings are illustrative only and that changes may be made in the specific construction illustrated. Furthermore, it is to be noted that the drawings are not to scale and dimensions may be adjusted as per manufacturer's specifications.

BRIEF DESCRIPTION OF THE DRAWINGS

Of various other objects, features and advantages of the present invention will become fully appreciated that the same becomes better understood when considered in conjunction with the accompanying drawings, in which like reference characters designate the same or similar for throughout the several views, and wherein.

DETAILED DESCRIPTION OF THE INVENTION

Figure 1:
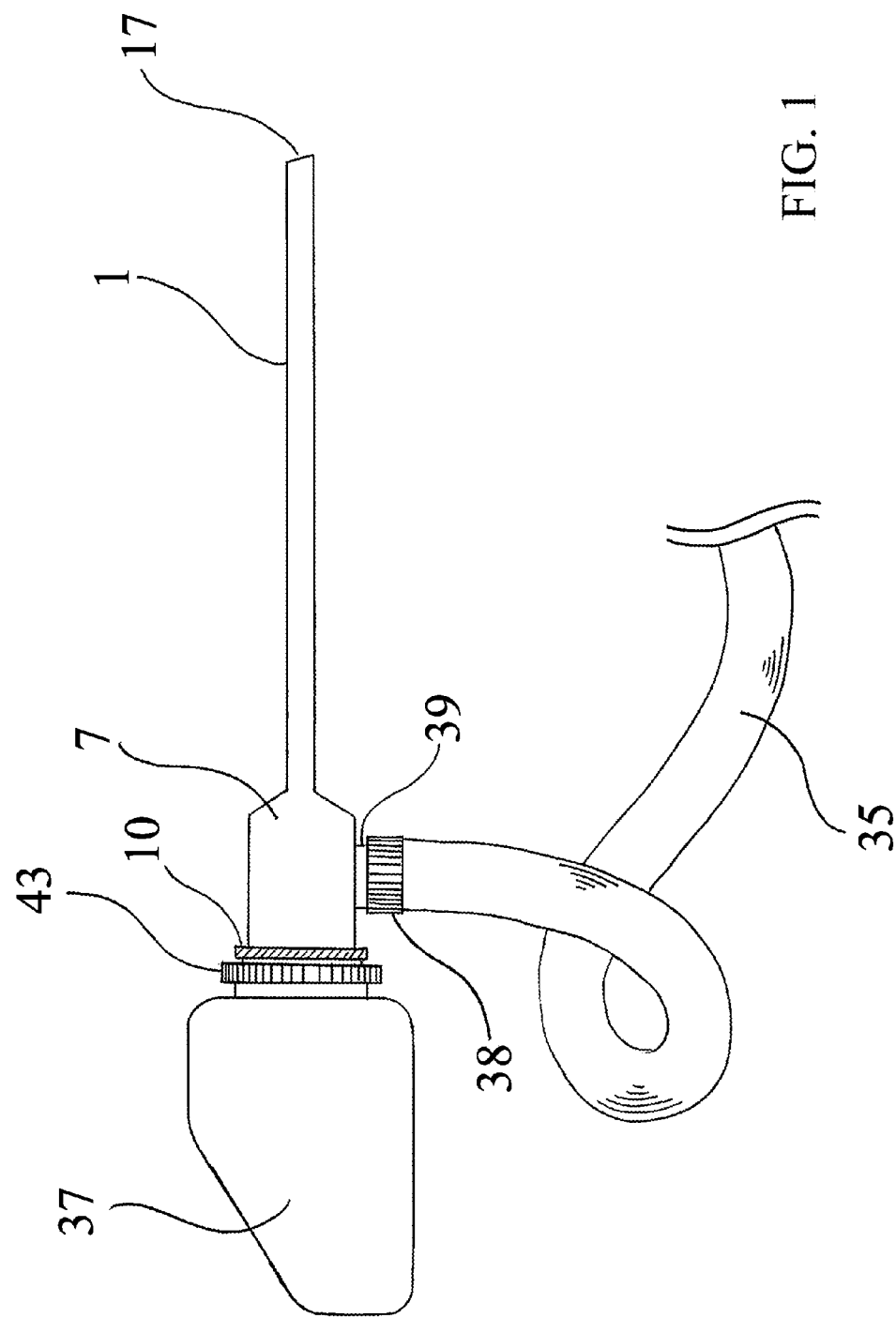
FIG. 1 is a perspective view of the endoscopy unit illustrating the single tubing cable attached to the arthroscope.

Turning now descriptively to the drawings, in which similar reference characters denote similar elements throughout the several views, the attached figures illustrate liquid cooled endoscopy unit having a single irrigation and suction tubing which also houses the light source power supply as well as the camera cord and power supply.

Figure 2:
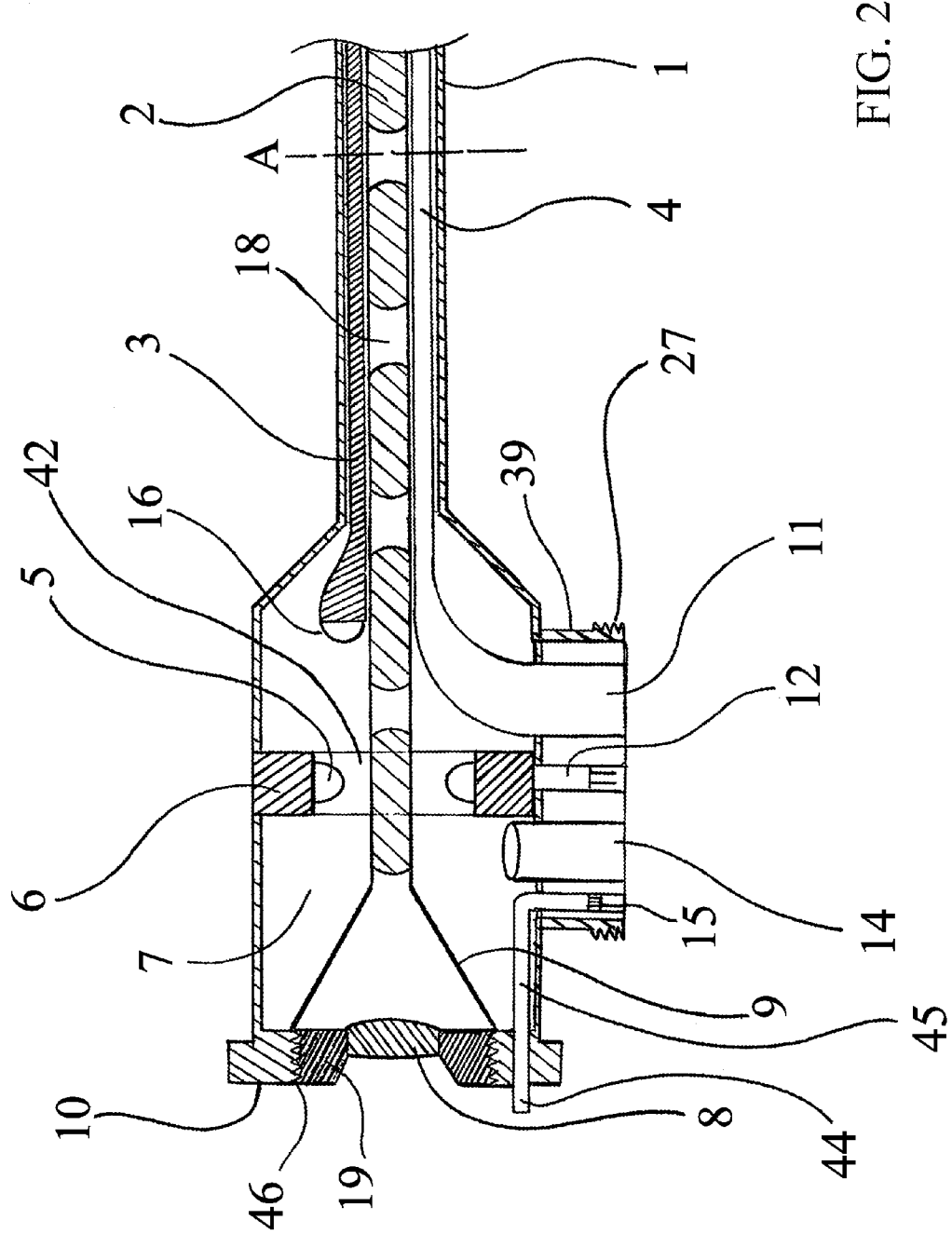
FIG. 2 is a sectional view of the proximal end of the arthroscope at the level of the cooling chamber showing the LED light source and the suction and irrigation channels.
Figure 6:
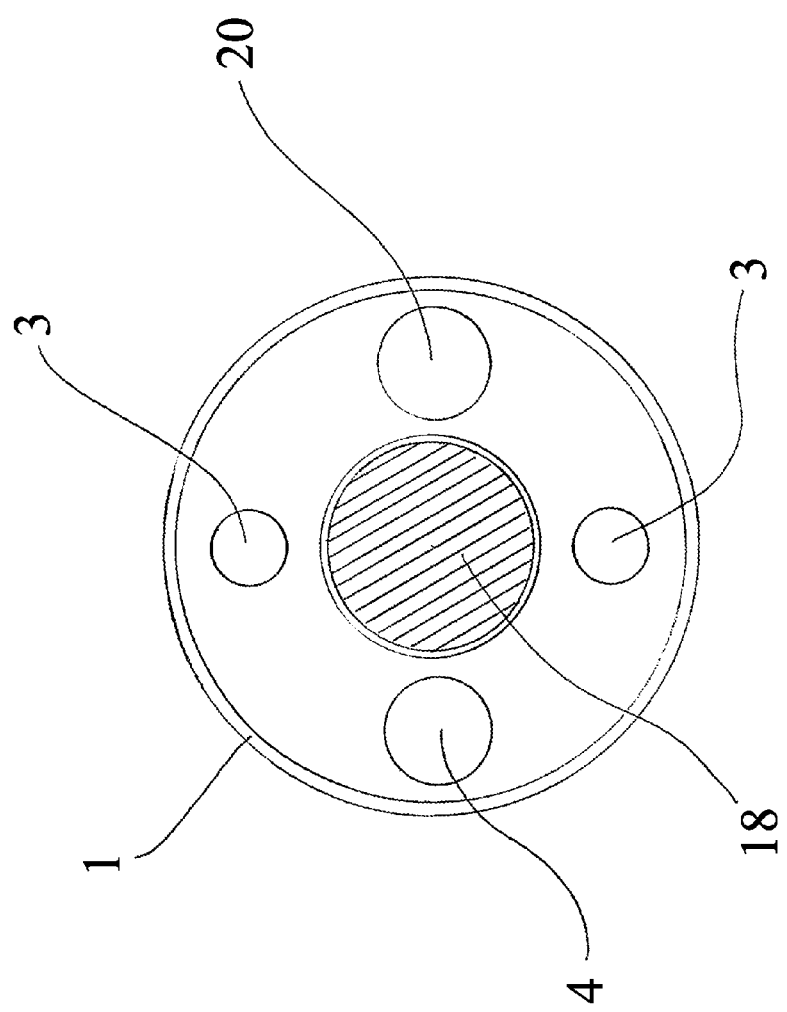
FIG. 6 is a cross sectional view of the arthroscope tube (A).

The liquid cooled endoscopy LED light source 5 as described comprises a plurality of LED light source 5 capable of providing sufficient white light for ease of viewing located within the cooling chamber 7. Said light source can also provide ultraviolet blue light on-demand for fluorescein endoscopy. The LED light sources 5 are embedded into a circular waterproof light source base 6 which provide a hollow central portion 42 which will allow the sterile irrigation fluid to go through (FIG. 2.) During its passage, the cool sterile irrigation fluid will come in direct contact with the LED light source 5 elements and reduce any excessive heat generated by the LED elements. The irrigation fluid will then be channeled to the distal tip of the arthroscope by irrigation channel 20 (FIG. 6).

Additionally, the LED light source is capable conveniently of emitting UV light for fluorescein endoscopy where one or more LED units are capable of producing UV light for the purpose of performing blue light fluorescein endoscopy. This inventive technique will highlight small articular and cartilaginous defect, which are not visible under conventional white light but will fluoresce vividly under blue light. This technique is readily used by ophthalmologists to detect corneal abrasions.

The circular waterproof light source base 6 is situated in the central portion of the cooling chamber 7 located at the proximal end of the arthroscope. Axially located is the optical tube 18 containing a variable number of Hopkins lenses 2. Proximally, the optical tube 18 is attached to the eyepiece 19 via optical cone 9. The ocular piece having a centrally located ocular lens 8 for transmission of the picture to a digital camera 37. The cooling chamber 7 provides a quick connect extension 39 situated to the side of said chamber, where irrigation inflow port 14, outflow port 11, power supply connection receptacle for the LED light source 12, and data and power connection receptacle 15 are situated. The port communicates with the suction channel 4 situated inside the shaft of the arthroscope. The optical tube 18 can be conveniently removed using threads 46 for ease of sterilization or optical maintenance.

The light generated by the LED elements will then be collected by lens 16 and transmitted to the distal tip of the arthroscope 17 via light channel 3 located in the shaft of the arthroscope.

A major improvement provided by the present invention is the elimination of multiple hoses and cables encumbering the surgical field, which may become entangled or slide off in the field and become contaminated.

The tubes, drains and cables are enclosed in a single non-slip tube 35 that is quickly and easily connected to the quick connect extension 39 of the arthroscope unit 1 (FIG. 1) Once the proximal end of the non-slip tubing 35 is inserted onto the quick connect extension 39 where each plug and tube is inserted into the corresponding port, the quick connect is then secured in place by tightening the locking nut 38. The proximal end of the inflow tube 29 will snuggly fit into the female irrigation port located at quick connect extension 39. The proximal end of the outflow suction tube 30 will be inserted into the corresponding female suction port 11. Similarly, power supply cable 33 will be inserted into its corresponding female power supply receptacle and camera and power data cable 32 will be inserted into its corresponding female data and power connection receptacle 15.

Figure 3:
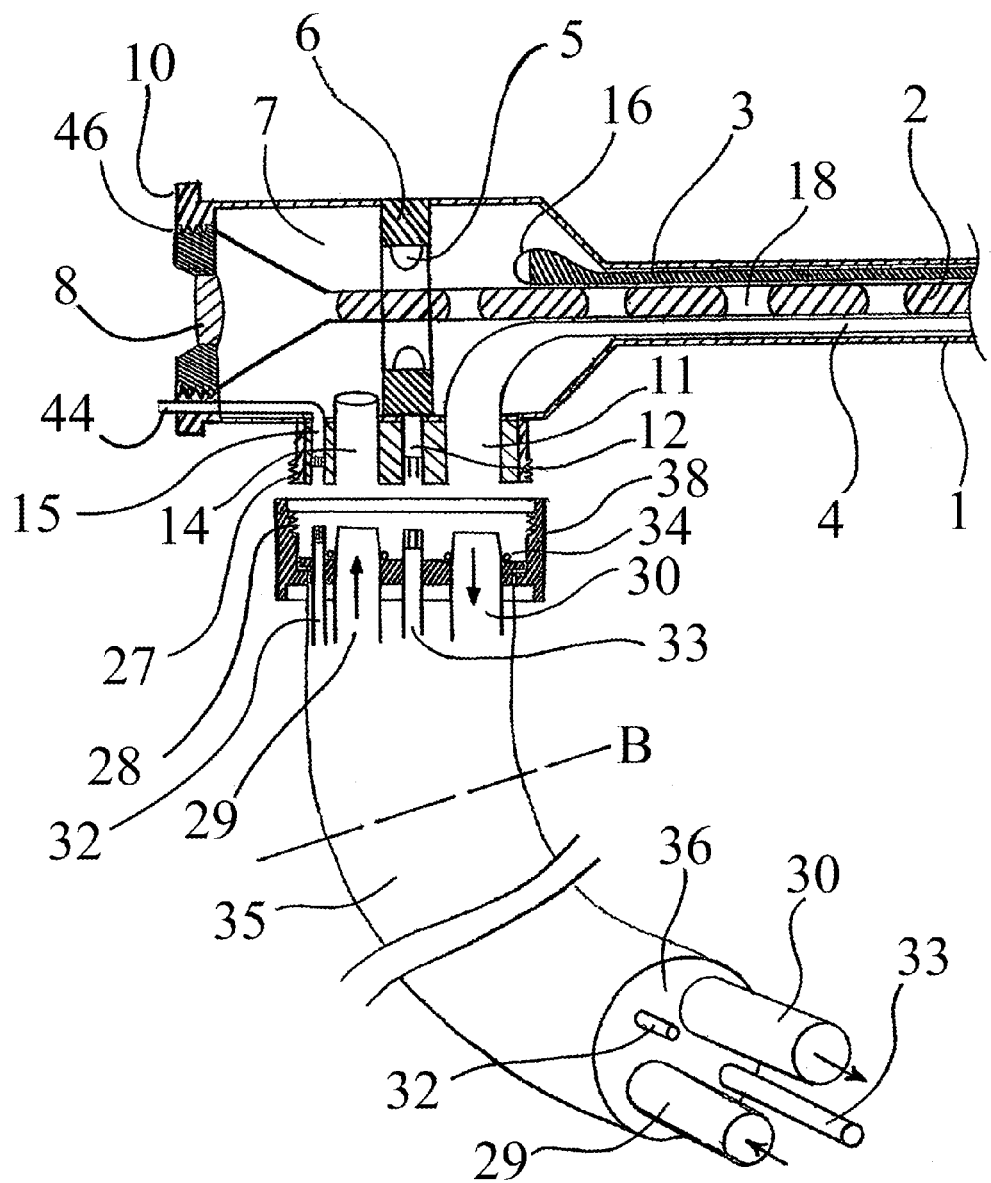
FIG. 3 is a section view of the Quick Connect with the single tubing cable.

Sealing rings 34 are situated around the base of each of the outflow and irrigation inflow ports to provide tight seals (FIG. 3). The sealing rings 34 may be made, for example, from silicone, rubber, or any other material(s) known to provide a tight seal.

Figure 4:
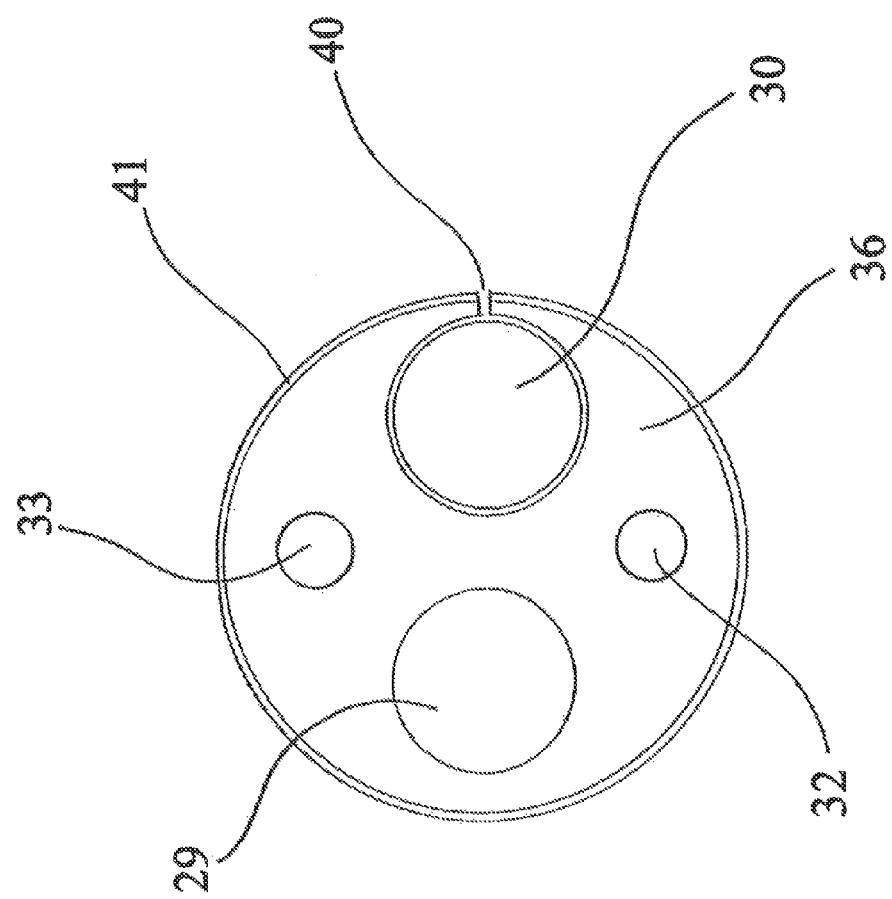
FIG. 4 is a cross Sectional view of the non-slip single tubing (B).

FIG. 4, shows a cross sectional view of the non-slip single tubing 35 where the body of the tube is constructed from soft open cell foam 36. In a different embodiment, the open cell foam 36 can be replaced with closed cell foam 36. A protective non-slip sheath 41 covers the entire body of the tubing cable. Said sheath can be constructed from a siliconized material with appropriate surface finish to prevent sliding off once placed onto the sterile drapes of the surgical field.

Yet in another embodiment, the single tubing housing can be constructed from malleable plastic tubing or conduit without the foam core. The suction irrigation and data/power supply cords are placed within the single plastic tubing.

The non-slip tube provides a longitudinal slice 40 situated along the entire length of the tubing at the level of the outflow suction tube 30 to allow easy and exchange incase the suction tubing is plugged by tissue debris.

Figure 5:
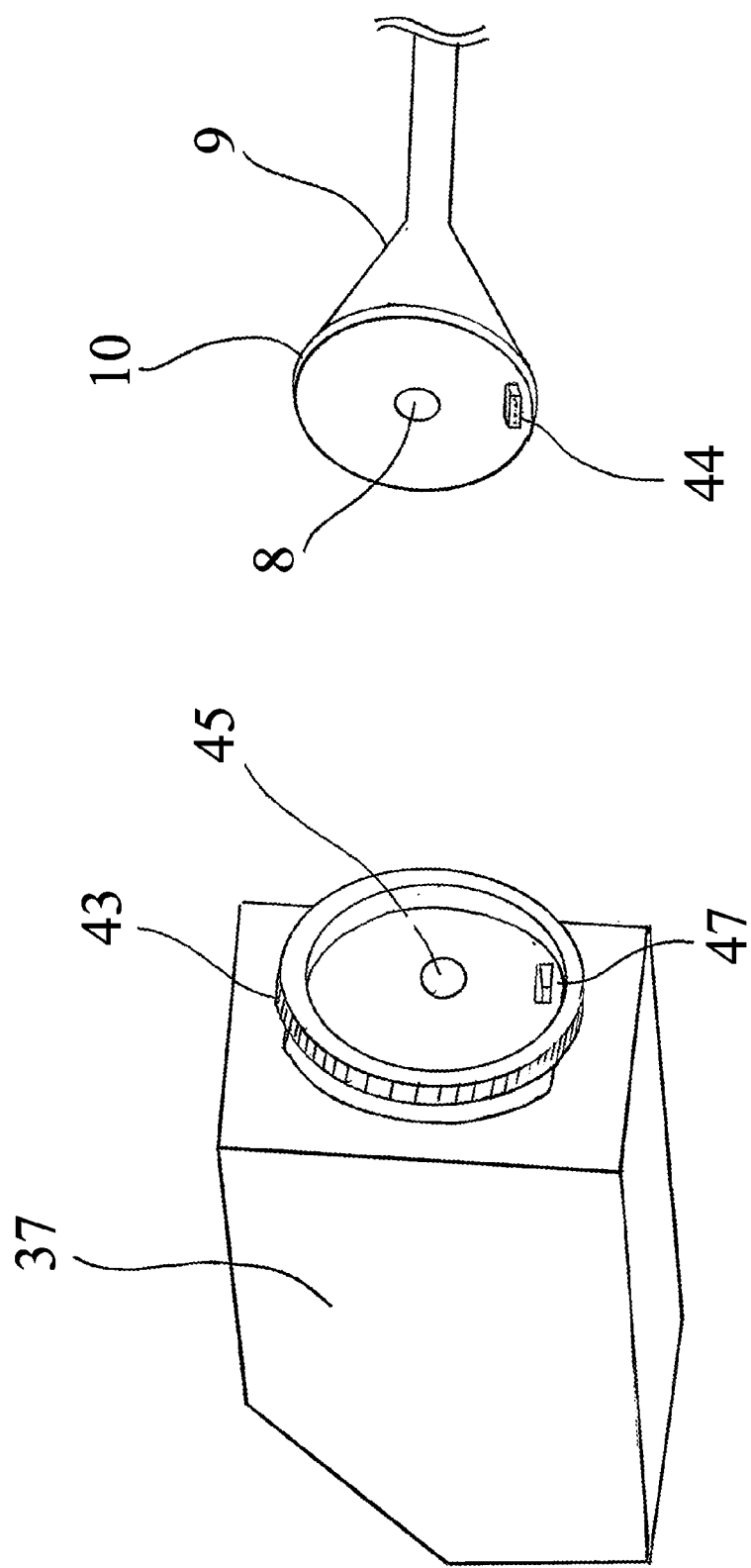
FIG. 5 is a perspective view of the quick connect between the camera and the arthroscope unit.

Referring to FIG. 5, the arthroscope is then attached to the digital camera 37 by inserting the proximal end of the arthroscope into the recess of the camera after aligning the camera data plug 44 and inserting it into the corresponding data receptacle 47 located onto the face of the digital camera 37. This will align the ocular lens 8 of the arthroscope with the camera lens 45. The arthroscope's locking rim 10 will then be firmly locked in place by the camera's locking rotating ring 43. Other locking mechanisms known in the art may be used.

The endoscopic imaging apparatus may be constructed from a light metallic alloy, a plastic or a composite material and may be disposable after a single use.

It is to be understood that the above-described arrangements are only illustrative of the application of the principles of the disclosure. Numerous modifications and alternative arrangements may be devised by those skilled in the art without departing from the spirit and scope of the disclosure and the claims are intended to cover such modifications and arrangements. Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A liquid cooled endoscopic imaging apparatus comprising:
   an endoscope having a proximal and distal portion, said endoscope comprising:
   a digital camera;
   a cooling chamber;
   a single housing tube;
   a quick connect extension having quick connect ingress and egress irrigation fluid ports to be detachably connected to said single housing tube;
   wherein the quick connect extension and the cooling chamber are in communication with the single housing tube;
   a circular waterproof light source base having a hollow central portion;
   one or more LED elements embedded into said circular waterproof light source base; and
   wherein said hollow central portion allows irrigation fluid to pass there through from the proximal to the distal portion of the endoscope and thereby dissipate heat generated from said one or more LED elements.

2. The liquid cooled endoscopic imaging apparatus of claim 1, wherein said one or more LED units are capable of producing UV light for the purpose of performing blue light fluorescence endoscopy.

3. The liquid cooled endoscopic imaging apparatus of claim 1, wherein said quick connect extension further comprises a locking nut for securing the proximal end of said single housing tube into said quick connect extension of the liquid cooled endoscopic imaging apparatus.

4. The liquid cooled endoscopic imaging apparatus of claim 1, wherein said single housing tube is made of flexible foam having an enveloping protective sheath made of non-slip material to avoid slipping of said single housing tube.

5. The liquid cooled endoscopic imaging apparatus of claim 4, wherein said non-slip material is selected from the group consisting of plastic, soft open cell foam and soft close cell foam.

6. The liquid cooled endoscopic imaging apparatus of claim 4, wherein said single housing tube has plural longitudinal channels each further housing one or more additional tubing channels.

7. The liquid cooled endoscopic imaging apparatus of claim 4, wherein said one or more additional tubing channels further comprise:
   an irrigation tube;
   a suction tube;
   a power and data supply cord for said camera; and
   a power and supply cord for said LED light source.

8. The liquid cooled endoscopic imaging apparatus of claim 1, further comprising:
   a camera data plug located on the proximal end of said endoscopic imaging apparatus; and
   a data receptacle located in said digital camera, for aligning said camera data plug and inserting it into said corresponding data receptacle.

9. A method for the thermal cooling of an integral LED light source contained within an endoscopic imaging apparatus, the method comprising:
   attaching a digital camera to an endoscope, wherein the endoscope comprises a cooling chamber and a single housing tube;
   coupling a quick connect extension having ingress and egress irrigation fluid ports to be detachably connected to the single housing tube, wherein the quick connect extension and the cooling chamber are in communication with the single housing tube;
   embedding one or more LED elements into a circular waterproof light source base having a hollow central portion;
   disposing said light source base within the cooling chamber of the endoscope; and
   passing sterile irrigation fluid through from a proximal to a distal portion of said endoscope through said hollow central portion, wherein said sterile irrigation fluid will come in direct contact with said LED elements thereby dissipating heat generated from said one or more LED elements.

10. The method as claimed in claim 9, wherein said irrigation fluid will then be channeled to the distal portion of the endoscope by an irrigation channel.

11. The method as claimed in claim 9, wherein one or more said LED units are capable of producing UV light for the purpose of performing blue light fluorescence endoscopy.

12. The method as claimed in claim 9, wherein attaching the camera to said endoscopic imaging apparatus comprises:
   inserting the proximal end of said endoscopic imaging apparatus into a recess of the digital camera after aligning a camera data plug and inserting it into a corresponding data receptacle located in said digital camera, so that an ocular lens of said endoscopic imaging apparatus is aligned with the camera lens.

13. The method as claimed in claim 12, wherein said attached camera is then firmly locked in place by a locking rotating ring disposed in the camera.

14. The endoscopic imaging apparatus of claim 1 constructed from a light metallic alloy, a plastic or composite material which may be disposable after a single use.

* * * * *